United States Patent [19]

Kesling

[11] Patent Number: 4,901,847
[45] Date of Patent: Feb. 20, 1990

[54] LIGATURE DISPENSER

[75] Inventor: Peter C. Kesling, LaPorte, Ind.

[73] Assignee: TP Orthodontics, Inc., Westville, Ind.

[21] Appl. No.: 306,840

[22] Filed: Feb. 3, 1989

[51] Int. Cl.[4] ............................................. A61B 19/02
[52] U.S. Cl. .................................... 206/63.5; 224/217; 433/49
[58] Field of Search ............... 224/217, 218, 219; 206/63.3, 63.5, 813; 433/49, 23, 18; 63/1.1

[56] References Cited

U.S. PATENT DOCUMENTS

| | | | |
|---|---|---|---|
| 902,109 | 10/1908 | Powell | 224/217 X |
| 2,209,210 | 7/1940 | Scholl | 206/813 X |
| 2,893,548 | 7/1959 | Carver, Jr. et al. | 206/63.3 |
| 2,970,379 | 2/1961 | Hardgrove | 63/1.1 X |
| 3,327,391 | 6/1967 | Malm | 206/63.5 |
| 3,902,245 | 9/1975 | Wolf | 224/219 X |
| 3,944,069 | 3/1976 | Eldridge, Jr. | 206/813 X |
| 4,008,802 | 2/1977 | Freitag | 206/63.3 |
| 4,038,753 | 8/1977 | Klein | 433/18 |
| 4,084,692 | 4/1978 | Bilweis | 224/217 X |
| 4,217,686 | 8/1980 | Dragan | 433/13 X |
| 4,412,820 | 11/1983 | Brummond et al. | 433/18 |
| 4,472,137 | 9/1984 | Barone | 433/3 |
| 4,717,057 | 1/1988 | Ponteous | 224/217 |
| 4,761,135 | 8/1988 | Steinkohl | 433/49 |

*Primary Examiner*—William Price
*Attorney, Agent, or Firm*—Lloyd L. Zickert

[57] ABSTRACT

A ligature dispenser for elastic ligatures used in orthodontic treatment of patients, and particularly for attaching an archwire to orthodontic brackets. The dispenser includes a hand-holdable curvate or flat body or supporting member on which are mounted a plurality of ligatures in standing up or laying down positions. The ligatures are releasably held on the supporting member by means of a suitable adhesive and/or by friction. A cover may be provided to enclose the supporting member and ligatures during shipping, storing and use.

26 Claims, 2 Drawing Sheets

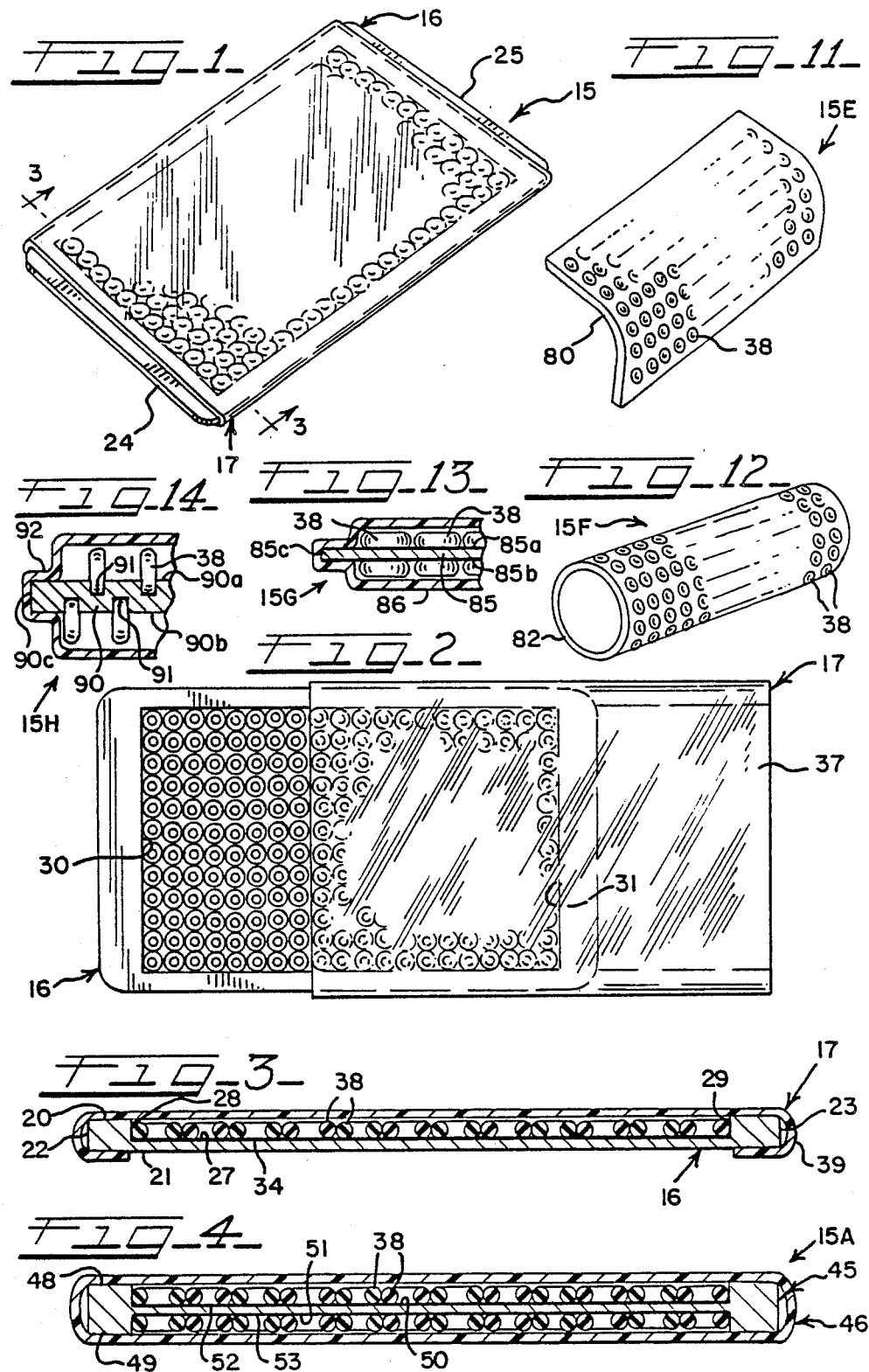

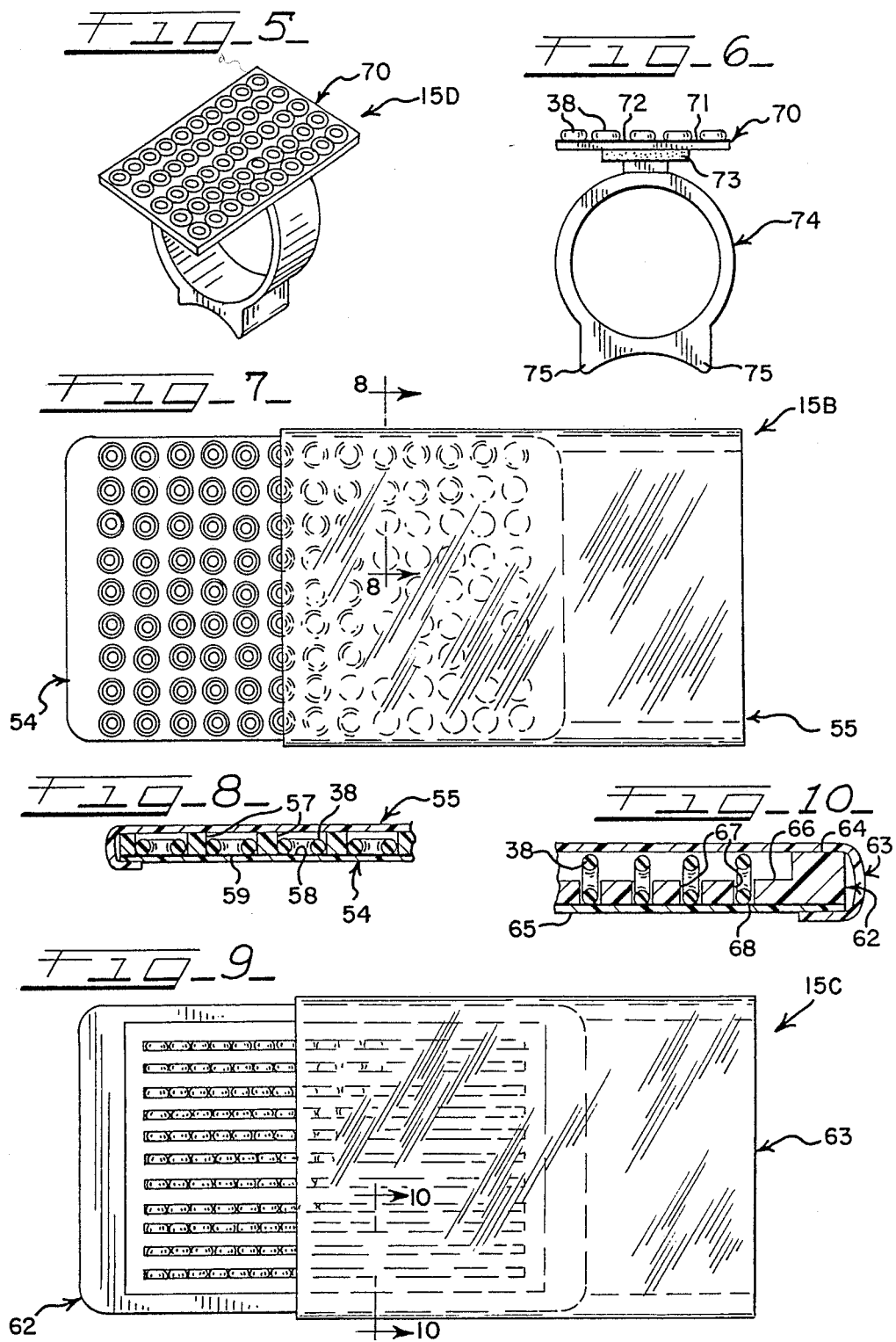

LIGATURE DISPENSER

DESCRIPTION

This invention relates in general to a ligature dispenser for elastic ligatures used in orthodontic treatment, and more particularly to a ligature dispenser for use by the orthodontist when desiring to apply one or more ligatures to an orthodontic system for orthodontically treating a patient, and still more particularly to a ligature dispenser that is particularly useful for dispensing ligatures one at a time with a suitable instrument that then applies the ligature to the orthodontic system of a patient, and still more particularly to a ligature dispenser that is constructed for the handling of elastic ligatures under materially improved hygienic conditions.

BACKGROUND OF THE INVENTION

Heretofore, there have been many types of elastic ligature dispensers, including the type that have held a plurality of individual elastic ligatures on a wire having one end formed for easy grasp by a person, and the type molded integrally with a support member that can be grasped by the hand and which requires separation of the ring from the support member by breaking a molded connection. Also, it has been well known to merely provide in a small plastic pouch a plurality of individual elastic ring-shaped ligatures that may be removed one at a time.

These ligature dispensers or packages have had one common defect in that they compromise the integrity of cleanliness and other hygienic conditions, inasmuch as they expose the ligatures to engagement by the hand of the user and to other contamination possibilities.

Moreover, where an instrument is used to apply the ligature to the orthodontic system, difficulty is often encountered in manipulating the instrument relative to the elastic in order to load the elastic on the instrument and properly engage the elastic so that it can thereafter be transferred and applied to an orthodontic system.

Another disadvantage of the molded dispensers which have the elastic ligatures molded to a support member is that difficulty may be encountered in breaking the molded connection to the support member.

SUMMARY OF THE INVENTION

The present invention provides an elastic ligature dispenser that obviates the difficulties heretofore known in prior dispensers in that the dispenser of the invention promotes the hygienic integrity of the ligature as it is being transferred from its package or dispenser to the orthodontic system in the mouth of a patient, and further that it is constructed so that it will be more easily useful with an instrument for applying the ligatures, and further that it is constructed to simultaneously give the maximum amount of capacity in a compact area to overall maximize the economics and convenience of using such ligatures.

The dispenser of the present invention is in the form of a curvate or card-shaped support member structured to adhesively and/or frictionally secure the ligature to the member but also allow it to be easily released without damage to the ligature. Suitable cover means can be provided to enclose the support member and the ligatures. While the form of the support member may take any desirable shape, it is preferably rectangular and may be provided with recessed areas that are common to several ligatures, or it may be provided with individual recessed surfaces for each ligature. It may also take a form that does not include any recesses. The card-shaped dispenser, being of credit-card size or smaller and of a stiffness to make it easily used with an instrument, may be comfortably held by the orthodontist during use and separation of the ligatures from the dispenser and transferring of same into the mouth of a patient to an orthodontic system. A suitable adhesive is provided to releasably secure the ligatures to the support. Suitable cover means may be provided over the support member and the ligatures to facilitate shipping and/or storage of the dispenser.

The dispenser of the invention may also be made in the form of a palette having an adhesive supporting surface for the ligatures and then being adaptable to be easily mounted onto a ring member which can be held by the thumb or finger of a person during use in extracting the elastics for use in an orthodontic system.

It is therefore an object of the present invention to provide a new and improved dispenser for elastic ring-shaped ligatures used in orthodontic systems which provides a relatively stiff member supporting the ligatures, thereby facilitating gripping by an instrument.

A further object of the present invention is in the provision of a new and improved elastic ring-shaped ligature dispenser for orthodontic systems which is particularly useful where an instrument is used to apply the ligature to the orthodontic system.

Another object of the present invention is to provide a new and improved dispenser for elastic ring-shaped ligatures capable of holding individual ligatures that may be removed one at a time by an instrument while maintaining relative hygienic integrity of the remaining ligatures.

A still further object of the present invention is in the provision of a new and improved dispenser for elastic ring-shaped ligatures having a greater capacity per area/volume than heretofore known dispensers of the type that are molded integrally with a support member.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of one form of the ligature dispenser according to the present invention;

FIG. 2 is a top plan view of the embodiment of FIG. 1 with the cover partially slid open for providing access to the ligatures.

FIG. 3 is an enlarged transverse sectional view taken substantially along line 3—3 of FIG. 1;

FIG. 4 is an enlarged transverse sectional view of an embodiment of the invention showing that ligatures can be provided on both sides of the support member;

FIG. 5 is a perspective view of another embodiment of the invention;

FIG. 6 is an end view of the embodiment of FIG. 5;

FIG. 7 is a top plan view of a still further embodiment of the invention where the support member includes cavities for each individual elastic ligature;

FIG. 8 is an enlarged partial cross-sectional view of the embodiment of FIG. 7 taken substantially along a line 8—8 of FIG. 7;

FIG. 9 is a top plan view of a still further embodiment of the invention with the cover partially removed to provide access to the interior where the ligatures are standing on their edges;

FIG. 10 is a greatly enlarged detailed transverse sectional view taken substantially along line 10–10 of FIG. 9;

FIG. 11 is a perspective view of a modified dispenser having a curvate supporting member for the ligatures;

FIG. 12 is a perspective view of a further modified dispenser having a cylindrically shaped supporting member for the ligatures;

FIG. 13 is a fragmentary cross section of a still further modified dispenser where the supporting member is of the type shown in FIGS. 5 and 6 and provided with ligatures on both sides and a cover; and FIG. 14 is a fragmentary cross section of a further modification of the invention where the supporting member is provided with slots sized to frictionally hold ligatures in upright positions.

DESCRIPTION OF THE INVENTION

Referring now to the drawings, and particularly to the embodiment shown in FIGS. 1 to 3, the ligature dispenser, generally indicated by the numeral 15, includes an elongated tray 16 forming the supporting member for a plurality of elastic ligatures, and a cover 17 slidably carried on the tray for covering the ligatures when they are supported by the tray. The supporting member 16 is preferably of a credit-card size in width and length and of a thickness to easily accommodate the ligatures when they are laying down in side-by-side relation. This size is easy to hold in the hand during use.

The supporting member 16 includes a top side 20, a bottom side 21 extending substantially parallel to the top side, opposed vertically extending side walls 22 and 23, and opposed substantially vertically extending end walls 24 and 25. A recessed area is provided in the top side defining a substantially flat bottom wall or surface 27, opposed substantially vertically extending side walls 28 and 29, and opposed substantially vertically extending end walls 30 and 31. The width and length of the recessed area are such as to be just less than the entire width and length of the tray to provide the greatest possible capacity for ligatures. However, it may be appreciated that the end walls may be eliminated or only one may be provided at one end.

An adhesive layer, coating or tape 34 is applied to the bottom wall or surface 27 on which the ligatures 38 are placed. The adhesive is of a type which releasably holds the ligatures to the supporting member such that the ligatures will not be displaced unless a force is applied to them to withdraw them from the surface. Thus, each ligature will stay in place until it is removed. Removal may be accomplished by a suitable instrument for handling the ligatures and which then would serve as an applicator to apply the ligature to an orthodontic system.

Preferably, the instrument would be of a type that would enter the center of a ligature and cause a stretching to facilitate removal and release from the adhesive.

The supporting member 16 may be made of any suitable material which would provide relative stiffness so that the supporting member will retain its shape while being easily held in the hand of a person for dispensing the ligatures and to provide a backing against which an instrument can apply nominal pressure without distorting the dispenser while gripping the elastic ring. For example, the supporting member may be made of a suitable rigid plastic and may be molded or otherwise formed. It also may be made of metal or even of a paper product.

The cover 17 includes a top panel 37 and hook-shaped sides 39 which overlie the opposite edges of the supporting member 16 as particularly seen in FIG. 3, and enable the cover to be slidably carried by the supporting member so that it may be slid on and off as desired and partially or fully opened. It is shown in the completely enclosed position in FIG. 1 where it overlies all of the ligatures. It is shown in partially open position in FIG. 2 so that access to some of the ligatures will allow their removal. It may be noted in FIG. 3 that the depth of the recessed area of the supporting member is slightly greater than the thickness of a ligature so that there is no interference between the ligatures and the cover member, thereby allowing the cover member to be easily slid along the supporting member.

It will be seen in FIG. 1 that the length of the cover member is slightly less than the length of the supporting member 16 so that at least one of the ends of the member will always be exposed, thereby facilitating the opening and closing of the dispenser.

It will be appreciated that the ligatures 38 are ring-shaped and preferably molded so that they have a round cross section although it will be appreciated that the ligatures may have a cross section of any geometrical shape. The ligatures are arranged in the recessed area of the supporting member in side-by-side and edge-to-edge relation and as seen in rows extending both longitudinally and transversely. This places them in a relation where they are most suitable for removal by use of an instrument which has gripping members extending into the center of a ligature and expandable to grip the ligature so that it can be removed and then directly applied to the orthodontic system. The dispenser stiffness provides a support for the ligatures during removal by an instrument.

Preferably the cover 17 is made of a transparent plastic, but it could be made of any desired material. When made of a transparent plastic, it is then easy to see the contents of the dispenser and to determine how many ligatures still remain in the dispenser from time to time.

When using the dispenser, it can easily be held in the hand of the user to have a ready supply of ligatures. Sliding the cover to one side opens the dispenser so that the ligatures are then available for removal, and they may be removed one at a time by a suitable instrument which then would be used to directly apply the ligature to the orthodontic system, and particularly for securing an archwire in an archwire slot of a bracket. When a desired number of ligatures has been removed, it is a simple matter to close the dispenser and maintain the hygienic integrity of the unused ligatures. It will also be appreciated that during usage of the dispenser, and when it is in open position, the hands of the user need not come into contact with the ligatures, as the fingers of the user would generally engage the opposite side edges of the dispenser. The credit-card size allows the dispenser to be easily held in the palm of the hand. Once, when the supply of ligatures has been exhausted and dispensed, the dispenser may then be disposed of.

The embodiment of FIG. 4 differs from the embodiment of FIG. 3 in that recessed areas are provided on both sides of the supporting member and the cover is constructed to enclose both recessed areas. The dispenser of this embodiment is generally indicated by the numeral 15A, and generally includes a double-sided tray forming a support member for the ligatures designated 45 and a sleeve-like cover 46. While this embodiment is only illustrated in cross-sectional view, it may be appreciated that it will have the same general rectangular configuration as the embodiment of FIGS. 1 to 3, and the cover 46 will similarly function to be slidably carried on the supporting member 45. It will be further appreciated that the supporting member 45 and the cover will be made of similar type materials as described above in connection with the embodiment of FIGS. 1 to 3.

The double-sided tray 45 includes a top side 48 and a bottom side 49, each of which includes a recessed area for receiving ligatures in laying down position. The recessed area in the top side 48 is defined by a substantially flat supporting surface 50 and opposed substantially vertically extending end and side walls, while the recessed area on the bottom side 49 is defined by a substantially flat surface 51, which likewise is bordered by substantially vertically extending side and end walls. As above mentioned, one or both end walls may be omitted. Again, the depth of the recessed area will be slightly greater than the depth of the ligatures in laying down position in order to prevent interference with the sliding of the cover 46 relative to the supporting member 45. The ligatures are adhesively secured to the respective substantially flat supporting surfaces by means of a suitable adhesive. For the upper recessed area, an adhesive layer or tape 52 will secure the ligatures in place to the supporting member, while in the lower recessed area an adhesive coating or tape 53 along the substantially flat surface will support and secure the ligatures in place. Again, the adhesive will function to retain the ligatures in the dispenser while allowing them to be easily removed by an instrument. Accordingly, the ligatures will not fall out when the tray is open and in an upside-down position.

The cover member 46 is sized to be slidably carried on the supporting member 45 and will have a length like that illustrated with respect to the cover member 17 in FIGS. 1 to 3 so that one or both ends of the supporting member will always slightly project from the cover. It will be appreciated that the dispenser 15A will have double the capacity for ligatures over the embodiment of FIGS. 1 to 3 and that it will differ by having a slightly greater depth by accommodating the lower recessed area. Further the cover will be in the form of a sleeve to completely enclose both sides of the tray.

The embodiment of FIGS. 7 and 8, generally designated by the numeral 15B, differs from the embodiment of FIGS. 1 to 3 in that each ligature is provided with its own recessed area or cavity and therefore not in contact with adjacent ligatures. Ligature dispenser 15B includes generally a tray in the form of a supporting member 54 and a cover 55. The supporting member 54 is provided with a plurality of cavities or recesses 57, each of which receives a ligature 38 and each of which also includes a bottom substantially flat surface or bottom wall 58 having thereon a coating of adhesive 59 for releasably securing the ligature in the cavity. The cavities are sized to complementarily receive the ligatures and therefore are circular in form and arranged in longitudinal and transverse rows adjacent to each and over substantially the entire surface of the supporting member. Alternatively, the cavities could be sized slightly smaller than the ligatures so that friction holds them in place rather than adhesive. While the cavities are circular in shape, they may be polygonally shaped if desired.

The operation of the ligature dispenser 15B will be the same as the operation of the ligature dispenser of FIGS. 1 to 3 in that the cover 55 will enclose all of the cavities when in closed position to maintain the hygienic condition of the ligatures. Then, when it is desired to use the ligatures, the cover will be partly opened to provide access to one or more rows of the ligatures so that an instrument can engage and remove a ligature for direct application to an orthodontic system in the mouth of a patient. Again, it will be understood that where an adhesive is used to releasably retain the ligatures in the cavities, it will be of a type that will leave a negligible residue on a removed ligature and which will allow easy release of the ligature from the dispenser upon applying a nominal force with an instrument that would enter the hole of the ligature and grip the ligature.

While it will be appreciated that the support member 54 may be molded in one piece, it could also be molded in two pieces wherein a first part would constitute a creditcard size member having a plurality of holes and a second part could be in the form of a thin sheet of plastic or the like that would be secured to one side of the first part in a suitable manner such as by use of double-face pressure-sensitive tape which would then provide an adhesive on the bottom walls of the cavities for the ligatures.

Referring now to the embodiment of FIGS. 9 and 10, which is generally designated by the numeral 15C, this embodiment differs from the embodiment of FIGS. 1 to 3 in that it is formed to present the ligatures in an upright or standing position. When the ligatures are on edge or in upright position, a hemostat or like instrument may be used to grip the upper portion of the ligature and remove it from the dispenser and thereafter apply the ligature to an orthodontic system. This embodiment includes a tray in the form of a supporting member 62, having a cover 63 of the same type as in embodiment of FIGS. 1 to 3. The supporting member 62 includes a top side 64 and a bottom side 65 and vertically extending side and end walls. A recessed area is formed in the top side 64 defined by a substantially flat surface or wall 66 and peripheral side and end vertical walls. A plurality of parallel aligned slots 67 are formed in the substantially flat surface 66 and are of a width approximately equal to the width of the ligature 38. The depth of the slot is about one-half the diameter of the ligature, although it may be deeper or shallower if desired. One or more of the surfaces of the slots has a coating of adhesive 68 to provide for releasably securing the ligatures in place in the slots when they are loaded with ligatures, or the side walls of the slots may frictionally retain the ligatures. The depth of the recessed area defined by the substantially flat surface 66 is such that it, along with the depth of the slot, will be slightly greater than the external diameter of the ligatures in order to allow the ligatures to stand up and not interfere with the slidable movement of the cover 63 relative to the supporting member during the opening and closing of the recessed area. The operation of the ligature dispenser 15C will be the same as the ligature dispenser of FIGS. 1 to 3 in that when it is desired to remove ligatures from the dispenser, the cover member may be slid relative to the supporting member so as to expose the desired number of ligatures, and then an instrument in the form of a hemostat may be used to remove the ligatures one at a time for application to an orthodontic system in the mouth of a patient. At the conclusion of using the desired number of ligatures, the dispenser then may be closed by sliding the cover member again over the recessed area containing the ligatures. Again, the length of the cover member can be slightly less than the length of the supporting member to facilitate the opening of the dispenser.

The embodiment of FIGS. 5 and 6 differs from the other embodiments in that it constitutes a dispenser generally designated by the numeral 15D, which can be mounted on the thumb or finger of the user during the time ligatures are needed for application to an orthodontic system. This embodiment includes a ligature supporting member 70 in the form of a palette having a substantially flat upper surface 71, coated with a suitable adhesive 72, and on which the ligatures 38 are mounted in laying down position and in side-by-side longitudinal and transverse rows. At the underside of the supporting member 70 a self-sticking adhesive pad 73 is suitably secured to the supporting member so that it may permit the mounting of the supporting member on a ring-shaped holder 74. A footed base is provided on the ring-shaped holder 74 to define cams 75 to facilitate rotating the ring by thumb pressure from below. Once the support of ligatures on the supporting member 70 is exhausted, it will be appreciated that the supporting member may be removed from the holder 74 by breaking the bond of the self-sticking adhesive pad 73, and then disposed of. Another palette full of ligatures may then be mounted on the holder, thereby permitting the holder 74 to be repeatedly used. It will be appreciated that no contact will be made by the user's hands with the ligatures in that the ligatures will be removed from the palette with an instrument and then directly applied to the orthodontic system for the patient.

The supporting member for the ligatures of the embodiment of FIGS. 9 and 10 may be made by molding it in an integral unit or it may be made in the same fashion as described relative to the embodiment of FIGS. 7 and 8 in that a first part would be molded which would comprise the upper part of the supporting member and define the recessed area and also the slots and then a laminate can be secured to the underside of the first part and define the base of the slots to form a completely integral structure. It will also be appreciated that both the embodiments of FIGS. 7 and 8 and FIGS. 9 and 10 may likewise have increased capacity by providing cavities on both sides in the fashion as illustrated in FIG. 4 wherein the thickness of the dispenser would be increased slightly but the capacity would be essentially doubled.

As above mentioned, the support surface for the ligatures may be curvate if desired. An illustration of such a modification is shown in FIG. 11, and another illustration is shown in FIG. 12. With respect to the modification in FIG. 11, it is generally identified as 15E and includes a curvate supporting member 80 in the form of a segment of a cylinder and on which are disposed a plurality of ligatures 38. While the surface on which the ligatures are mounted is curvate, it may be provided with cavities to receive the ligatures in a laying down position or in an upright position. Where the surface is plain and without cavities, it will be appreciated that the adhesive system heretofore mentioned will be used to releasably hold the ligatures to the supporting member. Where cavities are formed in the surface, adhesive may be used at the bottom of the cavities or the cavities may be sized to frictionally hold the ligatures in place.

Another modified dispenser is shown in FIG. 12 and generally designated by the numeral 15F, which includes a cylindrically formed surface on which the ligatures 38 may be received. Again, the ligatures may be held in place by a releasable adhesive or they may be received in cavities formed on the surface for frictionally receiving and holding the ligatures to the supporting member.

The embodiments of FIGS. 11 and 12 illustrate that the supporting member may be curvately formed, and it should also be appreciated that suitable cover means may be provided for the supporting members to protect the hygienic condition of the ligatures.

A further type of dispenser according to the invention is shown in FIG. 13 and generally designated by the numeral 15G. This dispenser includes a ligature supporting member 85 in the form of a flat plate and having upper and lower flat surfaces 85a and 85b on which ligatures 38 may be disposed in laying down position. In order to retain the ligatures in place, an adhesive coating would be applied to the surfaces 85a and 85b of the type previously mentioned. The placement of the ligatures would be in a similar fashion to the placement illustrated in FIGS. 1 and 2, where ligatures are in longitudinal and transverse rows but having the outside rows spaced inwardly from the side edges 85c of the supporting member so as to accommodate a cover means 86 which would be slidably carried on the supporting member. As previously mentioned, the cover means would be of a suitable transparent plastic so that the contents of the overall dispenser can be viewed when the cover is in closed position. Further, the cover means 86 is in the form of a sleeve having the opposite side edges pinched together in mating relation to the supporting member 85 but sized so that easy sliding action can be obtained between the cover and the supporting member. No adhesive coating would be in the pinched areas.

Where the conceptual construction of FIG. 13 would be desired for having ligatures received in upright standing position, the form of the dispenser would take the form illustrated in FIG. 14 and generally designated as 15H. This dispenser would include a supporting member 90 in the form of a flat plate having a plurality of longitudinally extending slots 91 in parallel relation t each other on both sides of the supporting member. It can be further seen in this embodiment that the slots on the upper side 90a are offset from the slots on the underside 90b so as to take advantage of the use of the space and to avoid any undue weakness in the supporting member. As in the embodiment of FIG. 13 where outer ligatures are spaced inwardly from the edges 85c to accommodate the lower guide portions, the slots 91 are also spaced inward from the side edges 90C so that an area on opposite sides can be provided for receiving in sliding relation guide portions of a cover 92. This cover will be in the form of a sleeve much like the cover of FIG. 13 where the opposite side edges are pinched together to coact with the supporting member 90. Further, the cover will operate in the same fashion in that when opening the dispenser, it will be slid in one direction relative to the supporting member to expose ligatures.

The ligatures 38 in the embodiment of FIG. 14 may be held in place by adhesive on any one or all of the surfaces of the slots 91 or the slots may be sized to frictionally hold the ligatures in place.

From the foregoing, it can be appreciated that the dispenser of the invention will be easy to use with an instrument for applying ligatures to an orthodontic system and will safeguard the hygiene of the ligatures by minimizing contamination in that the ligatures will be removed one at a time directly by the instrument from the dispenser and then directly applied to an orthodontic system in the mouth of a patient. Further, the cost of the dispenser will be nominal while providing an easy-to-use device in the handling of ligatures.

It will be understood that modifications and variations may be effected without departing from the scope of the novel concepts of the present invention, but it is understood that this application is to be limited only by the scope of the appended claims.

The invention is hereby claimed as follows:

1. A dispenser including a plurality of endless stranded elastic ligatures used in orthodontic treatment comprising, a supporting member having at least one surface on which said ligatures are disposed, and adhesive means on said supporting member surface only for releasably securing said ligatures to the member, whereby the ligatures may be easily removed one at a time by a suitable instrument leaving only a negligible residue on said ligature.

2. The dispenser of claim 1, wherein the ligatures are placed side by side on said supporting member.

3. The dispenser of claim 1, wherein the supporting surface is recessed.

4. The dispenser of claim 1, wherein the supporting surface is flat.

5. The dispenser of claim 1, wherein the supporting surface is curvate.

6. The dispenser of claim 1, wherein a recessed area is provided on the supporting member surface for receiving each ligature.

7. The dispenser of claim 6, wherein said recessed area is formed to receive the ligatures in parallel relation to the supporting member surfaces.

8. The dispenser of claim 6, wherein said recessed area is formed to receive the ligatures in vertical relation to the supporting member surface.

9. The dispenser of claim 1, which further includes cover means over the ligatures.

10. The dispenser of claim 9, wherein the cover means is transparent.

11. The dispenser of claim 1, wherein the supporting member includes a pair of opposed surfaces on which ligatures are disposed and releasably secured by adhesive.

12. The dispenser of claim 11, which further includes cover means over the ligatures.

13. The dispenser of claim 1, which further includes means for releasably securing the supporting member to a ring-shaped holder adapted to fit on the finger of a person.

14. The dispenser of claim 1, which further includes means for releasably securing the supporting member to a secondary supporting member.

15. The dispenser of claim 1, wherein complementarily shaped recesses are formed on said surface for receiving the ligatures.

16. The dispenser of claim 1, wherein elongated slots are formed on such surface for receiving the ligatures on their edges.

17. The dispenser of claim 9, wherein the cover means is transparent.

18. The dispenser of claim 9, wherein the cover means is formed to slide on and off said support member.

19. A dispenser including individual endless stranded elastic ligatures used in orthodontics to secure an archwire to orthodontic brackets, said dispenser comprising a supporting member of generally rectangular shape having a top side and a bottom side, said supporting member being of a stiffness to facilitate removal of the ligatures by an instrument, and adhesive means on both sides only for releasably securing the ligatures to said supporting member and leaving only a negligible residue on said ligatures when they are removed from the member.

20. A dispenser of claim 19, wherein the supporting member is of generally rectangular shape.

21. The dispenser of claim 19, which further includes cover means slidably carried on said supporting member to cover the ligatures.

22. The dispenser of claim 17, wherein the supporting member includes substantially flat surfaces recessed on both sides for receiving ligatures.

23. A dispenser including individual endless stranded elastic ligatures used in orthodontics to secure an archwire to orthodontic brackets said dispenser comprising a supporting member of generally rectangular shape having a top side and a bottom side, a plurality of slots in at least one side extending substantially the entire length of said supporting member adapted to receive ligatures in upright positions, the depth of the recessed area being about half the diameter of a ligature so that a ligature may easily be engaged by a hemostat for removal from the dispenser, and adhesive means in the slots only for releasably securing the ligatures to the supporting member and leaving only a negligible residue on said ligatures when they are removed from the member.

24. The dispenser of claim 23, which further includes cover means slidably carried by the supporting member to selectively cover the ligatures.

25. A dispenser including individual endless stranded elastic ligatures used in orthodontics to secure an archwire to orthodontic brackets, said dispenser comprising a supporting member of generally rectangular shape and having a top side and a bottom side, a plurality of ligature receiving cavities on at least one side for receiving ligatures that may thereafter be removed by a suitable instrument, and adhesive means in the cavity only for releasably securing the ligatures in the cavities and leaving only a negligible residue on said ligatures when they are removed from the member.

26. The dispenser of claim 25, which further includes cover means slidably carried by the supporting member to cover the ligatures, and wherein the depth of the cavities is such as to preclude contact between the cover means and the ligatures.

* * * * *

UNITED STATES PATENT AND TRADEMARK OFFICE
CERTIFICATE OF CORRECTION

PATENT NO.   :   4,901,847
DATED        :   February 20, 1990
INVENTOR(S)  :   Peter C. Kesling It is certified that error appears in the above-identified patent and that said Letters Patent is hereby corrected as shown below:

Col. 8, line 48, at the end of the line change "t" to --to--;

Col. 10, line 23, change "A" to --The--; and line 33, after "brackets" insert a comma (,).

Signed and Sealed this

Eleventh Day of December, 1990

*Attest:*

HARRY F. MANBECK, JR.

*Attesting Officer*     *Commissioner of Patents and Trademarks*